United States Patent [19]

Parissenti et al.

[11] Patent Number: 4,924,526
[45] Date of Patent: May 15, 1990

[54] PROTECTIVE VISOR

[75] Inventors: Stefano Parissenti; Lino Parissenti, both of Agordo, Italy

[73] Assignee: M.P.A. Meccanica Plastica Agordina S.p.A., Agordo, Italy

[21] Appl. No.: 179,735

[22] Filed: Apr. 11, 1988

[30] Foreign Application Priority Data

May 8, 1987 [IT] Italy .................. 41598 A/87
Jun. 29, 1987 [IT] Italy .................. 41624 A/87

[51] Int. Cl.⁵ .......... G02B 7/00; G02B 7/22; G02C 9/00; G02C 9/02
[52] U.S. Cl. ................... 2/13; 2/9; 2/15; 2/453
[58] Field of Search ........... 2/9, 13, 15, 424, 453, 2/443

[56] References Cited

U.S. PATENT DOCUMENTS

| | | | |
|---|---|---|---|
| 1,455,025 | 5/1923 | Kern-Jenny et al. | 2/15 X |
| 1,488,085 | 3/1924 | Zachara | 2/9 X |
| 1,582,164 | 4/1926 | Burstyn | 2/9 X |
| 2,342,982 | 2/1944 | Stern et al. | 2/9 |
| 2,388,626 | 11/1945 | Wilson | 2/13 X |
| 2,393,955 | 2/1946 | Baratelli et al. | 2/13 |
| 2,408,273 | 9/1946 | Sager | 2/13 X |
| 2,574,749 | 11/1951 | Mendelsohn | 2/13 X |
| 2,687,524 | 8/1954 | Mosher | 2/13 |
| 2,731,637 | 1/1956 | Kaplan et al. | 2/9 |
| 2,743,447 | 5/1956 | Young | 2/13 |
| 2,774,970 | 12/1956 | Du Bois | 2/9 |
| 2,875,670 | 3/1959 | Thornton | 2/13 X |
| 3,010,107 | 11/1961 | Lundblom | 2/13 |
| 3,298,031 | 1/1967 | Morgan | 2/9 |
| 3,531,188 | 9/1970 | LeBlanc et al. | 351/48 |
| 3,991,753 | 11/1976 | Viesca y Viesca | 2/9 X |

Primary Examiner—Werner H. Schroeder
Assistant Examiner—Jeanette E. Chapman
Attorney, Agent, or Firm—Guido Modiano; Albert Josif

[57] ABSTRACT

The visor comprises a transparent sheet of thermoformed plastic material. The sheet is cylindrical in shape and interchangeably upwardly associated with a monolithic supporting element. The monolithic element can be swivelling or fixed and is associable with the front part of a frame by means of a coupling device. The elements rigidly associated with the frame, being part of the coupling devices, are not visible from the front part of said frame. The frame can be a spectacle frame.

14 Claims, 2 Drawing Sheets

PROTECTIVE VISOR

BACKGROUND OF THE INVENTION

The present invention relates to a protective visor.

It is generally known that doctors may be subject to risks of contamination during the examination of patients, no effective protection devices being currently available.

The fabric masks currently in use for the protection of the respiratory tract, in fact, offer no valid bacteriological protection, nor do they, conversely, protect the patient from the doctor's breath.

These disadvantages assume primary importance for dentists, since they constantly operate very close to the face of the patient being treated.

A visor for spectacles or supporting frames is disclosed in U.S. Pat. Application No. 07/107.738 by the same Applicants, but it is not free from disadvantages, such as a rather troublesome application to the spectacles.

SUMMARY OF THE INVENTION

The aim of the present invention is to provide a protective visor which is easily associable with a pair of spectacles or to a frame by means of adapted coupling devices.

An important object is to provide a protective visor the coupling devices whereof do not affect the aesthetics of the spectacles when said visor is not associated therewith.

Another important object is to provide a protective visor which is capable of completely protecting the face both frontally and laterally.

Another object is to provide a protective visor which constitutes a valid bacteriological and/or contamination protection.

Still another object is to provide a structure of a protective visor which is associable in any frontal position of spectacles and with any frame in plastic, metal or other material.

Not least object is to provide a structure of visor easy to use and characterized by a reduced number of elements mutually assemblable at low cost.

This aim, as well as these and other objects which will become apparent hereinafter, are achieved by a protective visor comprising an interchangeable transparent sheet in thermoformed plastic material upwardly associated with a monolithic supporting element, said monolithic element being associable with the front part of a frame by means of a coupling device.

BRIEF DESCRIPTION OF THE DRAWINGS

Further characteristics and advantages of the invention will become apparent from the detailed description of some embodiments thereof, illustrated only by way of non-limitative example in the accompanying drawings, wherein.

DESCRIPTION OF THE PREFERRED EMBODIMENTS

Figure 1:
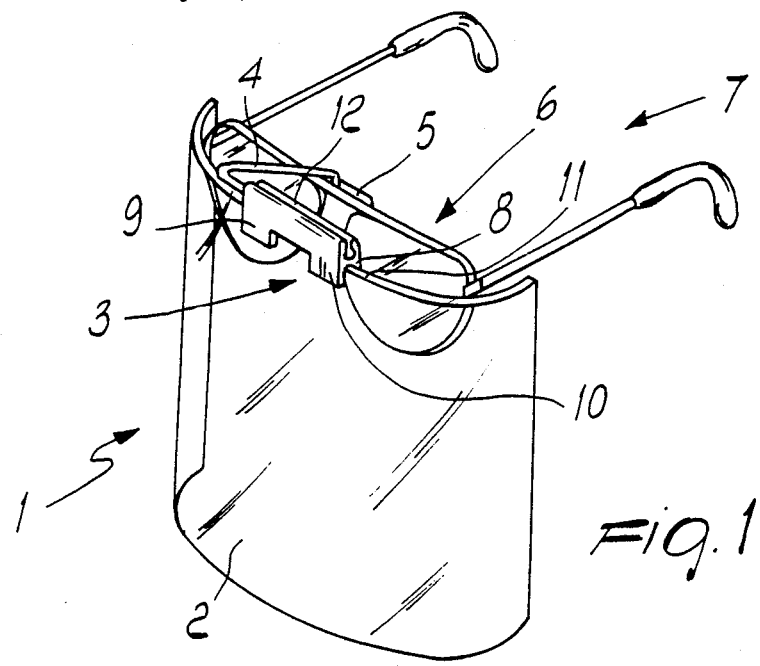
FIG. 1 is a perspective view of the visor according to the invention.

With reference to FIGS. 1-5, the protective visor according to the present invention is generally indicated by the reference numeral 1 and comprises a visor 2 constituted, for example, by a cylindrical transparent sheet in antifogging thermoformed plastic material, by a monolithic element 3 upwardly associated therewith and in turn associated, by a shaped metallic rod 4, by means of a coupling 5, with the front part 6 of a spectacle frame generally indicated at 7.

More in particular, said monolithic element 3 can be, for example, essentially parallelepipedal in shape and provided with a longitudinal hole 8 in which said rod 4 is inserted, with two lower tabs 9 and 10 longitudinally traversed by a vertical milling 11 and with another vertical milling 12 which extends in transverse cross section from the hole 8 to the upper surface.

The milling 11 is the seat of insertion and support of the visor 2.

Figure 2:
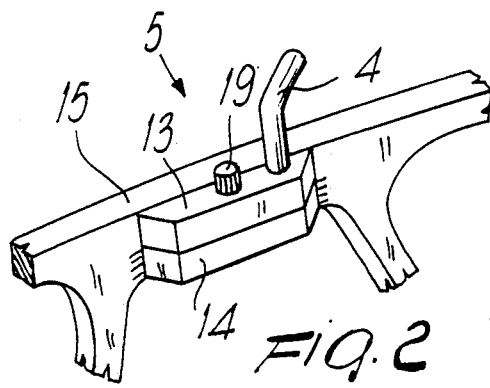
FIG. 2 is an enlarged perspective rear view of part of the frame of a pair of spectacles with a visor coupling device.
Figure 3:
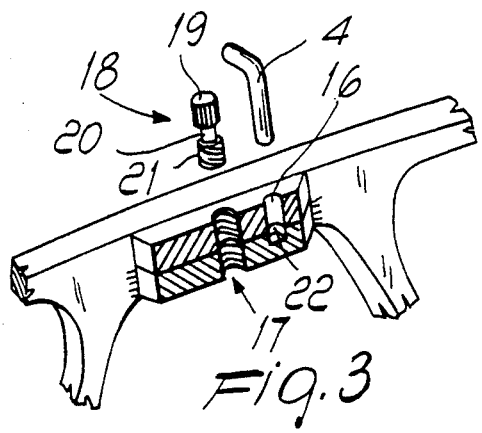
FIG. 3 is a perspective longitudinal sectional view of the coupling device of FIG. 2.

Said coupling 5, in a first embodiment illustrated in FIGS. 2 and 3, comprises two mutually superimposable trapezoidal elements, respectively 13 and 14, conveniently arrangeable longitudinally in the lower part of the connecting bridge 15 of the frame.

Said rod 4 is rigidly associated with said element 13, being inserted, protruding with its ends, in a transverse hole 16 with which said element 13 is transversely provided in lateral position, while said element 14 is rigidly associated, for example by welding, with the bridge 15.

A threaded hole 17 passes completely through the two coupled elements 13 and 14 and a coupling screw 18 is insertable therein, composed of a knurled cylindrical head 19, of a central cylindrical portion 20 equal in length to the thickness of said element 13 and of a threaded end 21 slightly greater in diameter than the portion 20 and equal in length to the thickness of said element 14.

The end of said rod 4, upon the coupling between said elements 13 and 14, locates itself in a deal hole 22 coaxial to said hole 16, thus acting as exact locator for the mutual positioning of said elements 13 and 14.

Figure 4:
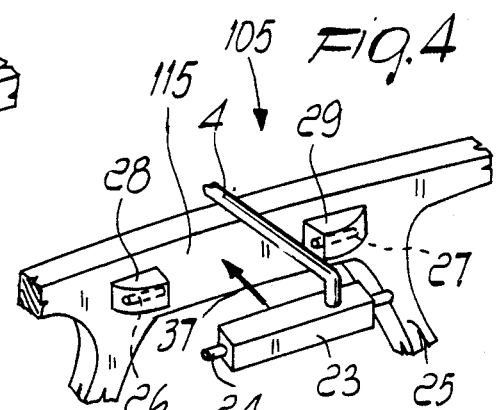
FIG. 4 is an enlarged perspective rear view of a spectacle frame having a visor coupling device according to another aspect of the invention.

Said coupling 5, in a second embodiment illustrated in FIG. 4 and generally indicated at 105, comprises a parallelepipedal element 23 longitudinally traversed by an axial cylindrical hole, not visible, in which are inserted, protruding at the ends, two metallic rods, respectively 24 and 25, mutually associated by an axial spring.

Said rods 24 and 25, by compression of the spring which connects them, are insertable in holes 26 and 27 with which two essentially trapezoidal tabs, respectively 28 and 29, which extend rearwardly with respect to said bridge now indicated at 115, are longitudinally provided.

Said parallelepipedal element 23 is rigidly associated with said rod 4 with a coupling of the type illustrated in the first embodiment.

Figure 5:
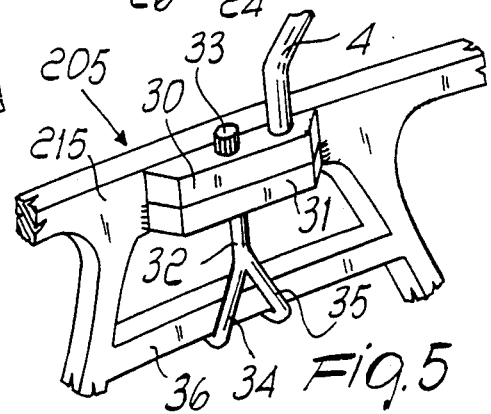
FIG. 5 is an enlarged perspective rear view of a spectacle frame having a visor coupling device according to a further aspect of the invention.

In a third embodiment of the coupling, illustrated in FIG. 5 and generally indicated at 205, the coupling is achieved between two trapezoidal elements, respectively 30 and 31, the first rigidly associated with said rod 4 and the second rigidly associated with the bridge now indicated at 215, by inserting a cylindrical rod 32 in a hole, not visible, which passes through both said elements, and a knurled cylindrical nut 33 is screwed to the upper end thereof.

The rod 32 is downwardly provided with two hooks 34 and 35 which couple to a crosspiece 36 arranged downwardly with respect to the bridge 215.

As to the operation of the first embodiment of the coupling device, in order to obtain the coupling of the structure of visor 1 to the frame 7 it is merely necessary to superimpose the element 13 on the element 14 and to tighten the screw 18 which, after use, will not come out of the element 13, being provided with the portion 20 which freely rotates in the upper portion of the hole 17.

As to the second embodiment of the coupling device, it is merely necessary to compress, by means of a tool, the two rods 24 and 25, then move, in the direction of the arrow 37 of FIG. 5, the parallelepipedal element 23 closer to the tabs 28 and 29, then release said rods 24 and 25 so that they insert in the holes 26 and 27.

Finally, as to the third embodiment of the coupling device, to associate the structure of visor 1 to the frame 7 it is merely necessary to superimpose the element 30 associated with said visor on the element 31 protruding from the front bridge of said frame, then insert the cylindrical rod 32 in the hole which passes through both elements and screw the nut 33 taking care that the two hooks 34 and 35 perfectly couple to the crosspiece 36.

Naturally the abovesaid coupling devices can be positioned on any front part of a spectacle frame, regardless of the material of which the same is constituted.

The visor 2 furthermore can have any convenient shape and cover fully or partly the face of the user in both forward and lateral extension.

Figure 6:
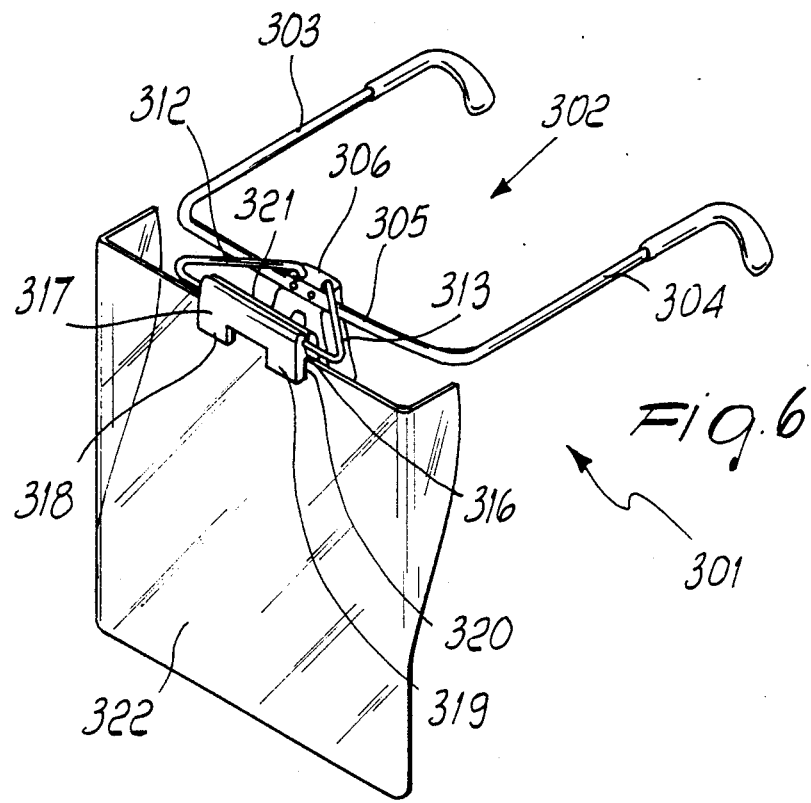
FIG. 6 is a perspective view of a visor according to a further aspect of the invention.
Figure 7:
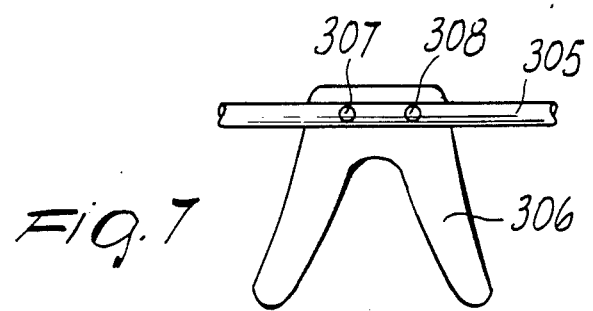
FIG. 7 is an enlarged front view of a detail of the visor showing the nose resting support.
Figure 8:
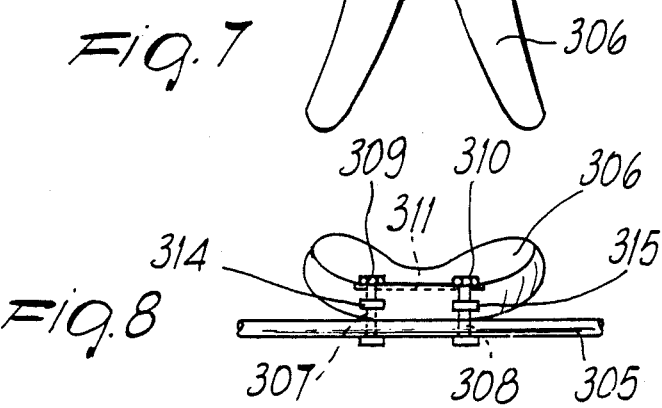
FIG. 8 is a top view of the support of FIG. 7.

With reference to FIGS. 6–8, the protective visor is generally indicated by the reference numeral 301, and is composed of a framework 302 comprising two small rods, respectively 303 and 304, joined at the sides of a front portion 305.

With said front portion 305 there is associated a nose resting support 306 which, according to the present embodiment of the invention, is made of plastics, but may conveniently be in any material.

The association between said support 306 and the framework 302 is achieved by means of two screws, respectively 307 and 308, fixed by means of two small bolts 309 and 310 to a small metallic plate 311 located rearwardly with respect to said support 306.

Two metallic rods, respectively 312 and 313, conveniently shaped, are inserted with their ends with rectangular cross section, not visible in FIG. 6, in two vertical dead holes 314 and 315 present in the support 306 and shaped complementarily thereto.

The opposite ends of said rods 312 and 313 are inserted in a hole 316 which longitudinally traverses a monolithic element 317 essentially parallelepipedal in shape.

Said monolithic element is downwardly provided with two tabs 318 and 319 longitudinally traversed by a vertical milling 320 provided with bevelings.

Another vertical milling 321 longitudinally traverses said monolithic element 317 extending in transverse cross section from the hole 316 to the upper surface.

The milling 320 is the insertion and support seat of an interchangeable visor 322 in transparent material shaped so as to also constitute a lateral protection for the face.

The bevelings with which said milling 320 is provided are used to facilitate the insertion of the visor 322.

According to the invention, the framework 302 can conveniently be in metallic material, in plastic material, in any combination between plastic and metallic material or in any other material.

In another embodiment of the visor, the monolithic element 317 can be supported by a single rod associated with the framework 302 or can directly constitute an extension of the support 306.

The possibility is provided of adding to the visor a shaped element which completely protects the face even upwardly and laterally.

The possibility is furthermore provided to couple to the lateral rods an elastic, so as to completely embrace the head, preventing the possibility of unwanted movements of the structure during work.

From what has been described above, it is apparent that the invention achieves the intended aim and objects, since the visor according to the invention can be used by anyone requiring protection of the face.

Said visor also assumes an accident-prevention role in case of its use for protection during operations which entail the formation of splinters, shavings or small harmful objects.

Said type of visor can also be used by cyclists or motorcyclists for protection against dust or insects.

Furthermore, the coupling devices are structured so that when the visor is not associated with the frame said spectacles are not distinguishable from others.

If required said spectacles, if deprived of their lenses, may become a visor-holder.

The invention thus conceived is susceptible to numerous modifications and variations, all of which are within the scope of the inventive concept, thus for example in the first embodiment of the coupling the hole which passes through the two coupling elements may be dead and various locator elements may be used for the exact mutual positioning of said two elements, furthermore all the details may be replaced with other technically equivalent elements.

In practice the materials employed, as well as the dimensions, may be any, according to the requirements.

We claim:

1. A protective visor comprising an interchangeable transparent sheet in a thermoformed plastic material upwardly associated with a monolithic supporting element, said monolithic element being associated by means of a coupling device with a front part of a spectacle frame, said spectacle frame having a connecting bridge, wherein said coupling device comprises at least two elongated elements mutually superimposable and arrangeable longitudinally in the rear part of said connecting bridge, a first one of said elements being rigidly associated with a rod, said rod being coupled with said monolithic element, a second one of said elements being rigidly associated with said bridge, both said elements being completely traversed by a thread hole in which a coupling screw is insertable.

2. A visor according to claim 1, wherein said transparent sheet in thermoformed plastic material has a cylindrical shape so as to cover the face of the user at least partially.

3. A visor according to claim 1, wherein said monolithic element is downwardly provided with two tabs longitudinally traversed by a vertical milling provided with bevelings.

4. A visor according to claim 1, wherein said rod associated with said monolithic element is inserted in a hole which passes through said first element, said rod protrudes therefrom with an end which acts as an exact locator for a mutual positioning of said first element with said second element, said second element being provided with a dead hole for the accommodation of said end.

5. A protective visor comprising an interchangeable transparent sheet in a thermoformed plastic material upwardly associated with a monolithic supporting element, said monolithic element being associable by means of a coupling device with a front part of a spectacle frame, said spectacle frame having a connecting bridge, wherein said coupling device comprises a parallelepipedal element longitudinally traversed by an axial cylindrical hole in which are inserted at least two small metallic element rods mutually associated by an axial spring, said element rods being insertable, by means of compression of said axial spring, into holes provided in two substantially trapezoidal tabs associated with and extending from said connecting bridge, said parallelepipedal element being coupled to a metallic connecting rod associated with said monolithic element.

6. A visor according to claim 1, wherein said transparent sheet in thermoformed plastic material has a cylindrical shape so as to cover the face of the user at least partially.

7. A visor according to claim 1, wherein said monolithic element is downwardly provided with two tabs longitudinally traversed by a vertical milling provided with bevelings.

8. A protective visor comprising an interchangeable transparent sheet in a thermoformed plastic material upwardly associated with a monolithic supporting element, said monolithic element being associable by means of a coupling device with a front part of a spectacle frame, said spectacle frame having a connecting bridge, wherein said coupling device comprises two superimposable trapezoidal elements, a first one thereof being rigidly associated with a connecting rod associated with said monolithic element, a second one thereof being rigidly associated with said connecting bridge, both said elements being traversed by a cylindrical rod inserted in a cylindrical hole which passes through said elements and at an upper protruding end of said cylindrical rod, a knurled cylindrical nut is screwed, said cylindrical rod being downwardly provided with two hooks which couple to a crosspiece arranged downwardly with respect to said connecting bridge.

9. A visor according to claim 8, wherein said transparent sheet in thermoformed plastic material has a cylindrical shape so as to cover the face of the user at least partially.

10. A visor according to claim 8, wherein said monolithic element is downwardly provided with two tabs longitudinally traversed by a vertical milling provided with bevelings.

11. A protective visor comprising an interchangeable transparent sheet in a thermoformed plastic material upwardly associated with a monolithic supporting element, said monolithic element being associable by means of a coupling device with a front portion of a frame, said frame comprising two small rods joined at the sides of said front portion, a nose resting support associated with said frame by means of at least two screws inserted into holes with parallel axes which pass through said frame and are fixed by means of two small bolts to a small metallic plate located rearwardly with respect to said nose support, wherein said coupling device comprises at least two shaped metallic rods, each having an end inserted into a longitudinal hole which traverses said monolithic element and each having another end, provided with traverse holes for simultaneously inserting said screws which traverse said support, inserted into complimentarily shaped vertical holes provided in said nose support.

12. A visor according to claim 11, wherein said transparent sheet in thermoformed plastic material has a cylindrical shape so as to cover the face of the user at least partially.

13. A visor according to claim 11, wherein said monolithic element is downwardly provided with two tabs longitudinally traversed by a vertical milling provided with bevelings.

14. A visor according to claim 11, wherein said nose resting support is made of plastic material.

* * * * *